United States Patent
Graumann et al.

(10) Patent No.: US 7,340,291 B2
(45) Date of Patent: Mar. 4, 2008

(54) MEDICAL APPARATUS FOR TRACKING MOVEMENT OF A BONE FRAGMENT IN A DISPLAYED IMAGE

(75) Inventors: Rainer Graumann, Hoechstadt (DE); Axel Hebecker, Spardorf (DE); Joachim Hey, Bornheim (DE)

(73) Assignee: Siemens Aktiengesellschaft, Munich (DE)

( * ) Notice: Subject to any disclaimer, the term of this patent is extended or adjusted under 35 U.S.C. 154(b) by 626 days.

(21) Appl. No.: 10/615,527

(22) Filed: Jul. 8, 2003

(65) Prior Publication Data

US 2004/0024310 A1 Feb. 5, 2004

(30) Foreign Application Priority Data

Aug. 5, 2002 (DE) .............................. 102 35 795

(51) Int. Cl.
- *A61B 1/00* (2006.01)
- *A61B 1/04* (2006.01)
- *A61B 5/05* (2006.01)
- *A61B 6/00* (2006.01)

(52) U.S. Cl. .................. 600/427; 600/103; 600/109; 600/117; 600/407; 600/425; 600/426; 378/20

(58) Field of Classification Search ............... 600/407, 600/409
See application file for complete search history.

(56) References Cited

U.S. PATENT DOCUMENTS

| | | | |
|---|---|---|---|
| 6,167,145 A * | 12/2000 | Foley et al. ............... 382/128 |
| 6,285,902 B1 * | 9/2001 | Kienzle et al. ............. 600/427 |
| 6,470,207 B1 * | 10/2002 | Simon et al. ............... 600/426 |
| 6,491,429 B1 * | 12/2002 | Suhm ......................... 378/205 |
| 6,498,944 B1 * | 12/2002 | Ben-Haim et al. .......... 600/407 |
| 6,560,354 B1 * | 5/2003 | Maurer et al. .............. 382/131 |
| 6,801,801 B1 * | 10/2004 | Sati ............................ 600/429 |
| 6,895,268 B1 | 5/2005 | Rahn et al. |
| 2001/0055016 A1 | 12/2001 | Krishnan |
| 2003/0073901 A1 * | 4/2003 | Simon et al. ............... 600/424 |
| 2004/0022424 A1 | 2/2004 | Seissler et al. |

FOREIGN PATENT DOCUMENTS

DE    100 57 023    6/2002

OTHER PUBLICATIONS

"OP-Handbuch, Grundlagen Instrumentation OP-Ablauf," Middelanis et al (1995) pp. 159-160.

* cited by examiner

Primary Examiner—Brian L. Casler
Assistant Examiner—James Kish
(74) Attorney, Agent, or Firm—Schiff Hardin LLP

(57) ABSTRACT

A medical apparatus has a data processing device for storing an image dataset of the body of a subject and a navigation system for determining the position of a medical instrument relative to the body of the subject. At least one bone fragment is shown in the image represented by the image dataset, the image of the one bone fragment being segmented with a computer. The bone fragment is to be grasped and set with the medical instrument. The data processing device also determines the modified position of the bone fragment on the basis of the position of the medical instrument relative to the body of the subject determined with the navigation system, and displays the modified position in the image.

17 Claims, 1 Drawing Sheet

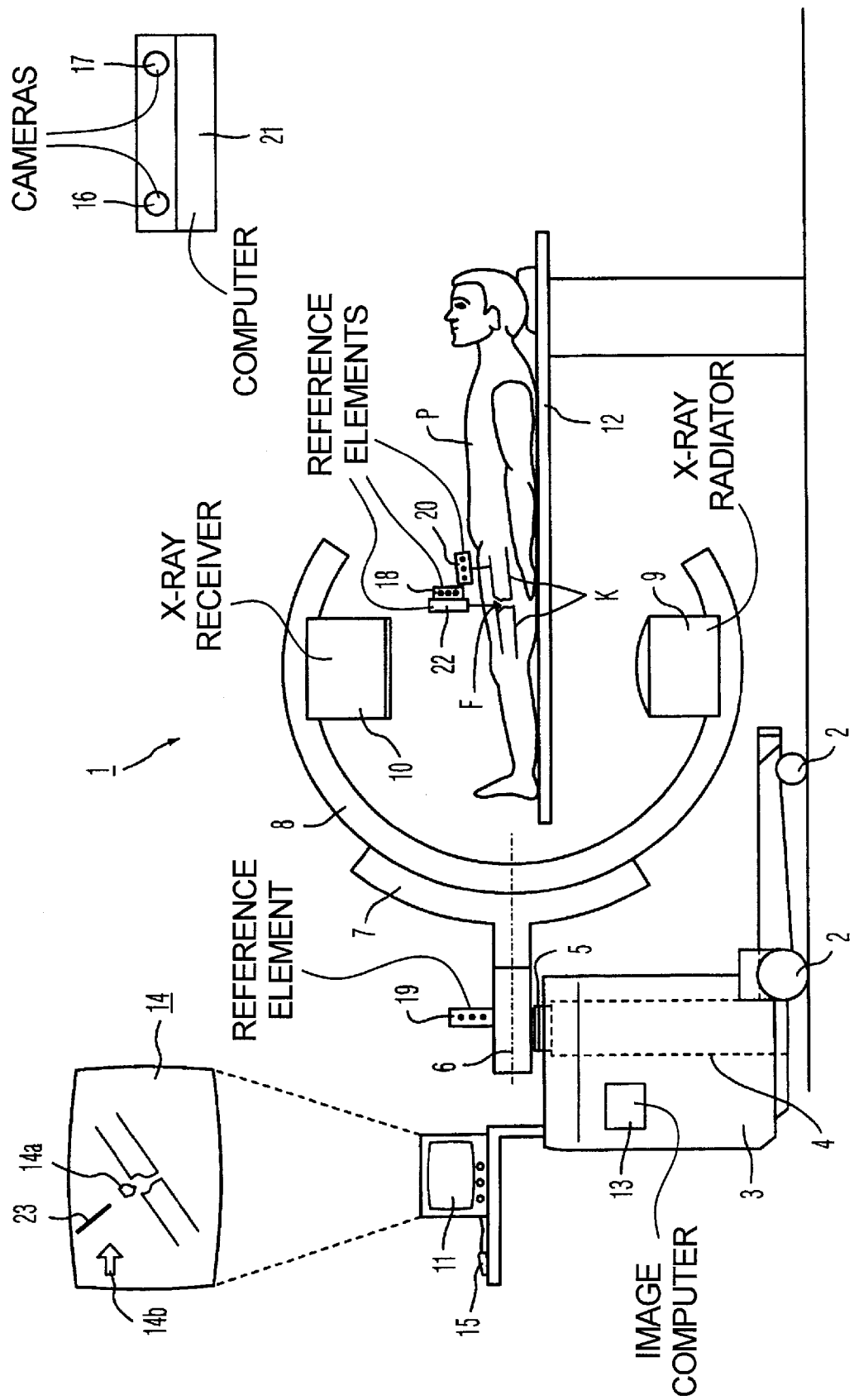

ated in German OS 199 51 501. For example, the image dataset—which is specifically a three-dimensional image dataset—of the region of interest of the body of a patient is produced with an X-ray device. A surgeon introduces the medical instrument into the body of the patient, particularly, in a minimally invasive procedure. A position sensor of the navigation system is arranged at the medical instrument, so that the navigation system identifies the position, i.e. the location and orientation, of the medical instrument relative to the body of the patient. An image of the medical instrument can be subsequently mixed into the image represented by the image dataset on the basis of the position determination, i.e. on the basis of a determination of the position coordinates of the medical instrument. The image can be presented, for example, on a monitor.

MEDICAL APPARATUS FOR TRACKING MOVEMENT OF A BONE FRAGMENT IN A DISPLAYED IMAGE

BACKGROUND OF THE INVENTION

1. Field of the Invention

The present invention is directed to a medical apparatus of the type having a data processing device for storing an image dataset of the body of a living subject, having a medical instrument for introduction into the body of the subject, and a navigation system for determining the position of the medical instrument relative to the body of the subject.

2. Description of the Prior Art

A medical apparatus of this type is disclosed in German OS 199 51 501. For example, the image dataset—which is specifically a three-dimensional image dataset—of the region of interest of the body of a patient is produced with an X-ray device. A surgeon introduces the medical instrument into the body of the patient, particularly, in a minimally invasive procedure. A position sensor of the navigation system is arranged at the medical instrument, so that the navigation system identifies the position, i.e. the location and orientation, of the medical instrument relative to the body of the patient. An image of the medical instrument can be subsequently mixed into the image represented by the image dataset on the basis of the position determination, i.e. on the basis of a determination of the position coordinates of the medical instrument. The image can be presented, for example, on a monitor.

The image dataset can be pre-operatively produced, for example with a computed tomography apparatus. For mixing in the image of the medical instrument it is necessary to undertake a spatial transformation of the coordinates (with respect to a first coordinate system) of the position sensor of the navigation system arranged in a defined way at the medical instrument into the spatial coordinates of the image of the patient acquired with the computed tomography apparatus and employed for the navigation. This transformation is referred to as registration. Markers can be attached to the patient for the registration. The positions of the markers are identified in the first coordinate system, with the position sensor of the navigation system and are identified (for example, by manual entry with an input device) in the coordinate system of the image stored in the data processing device, which was acquired with the computed tomography apparatus and is employed for navigation. Ultimately, a transformation can be calculated from the two points sets of the markers identified in the first coordinate system and in the coordinate system of the image employed for navigation. The transformation transforms the positions of the medical instrument, acquired in the first coordinate system with the position sensor of the navigation system, into the coordinates of the image during the navigation.

If the image dataset of the body of the patient is intraoperatively produced, for example with an X-ray device as likewise disclosed in German OS 199 51 502, then the navigation system can be implemented such that, in addition to determining the position of the medical instrument, ii also determines the position of the X-ray device, so that a registration for mixing the image of the medical instrument into the image of the body of the patient can be omitted.

Bone fragments that arise, for example, in the case of splinter fractures can be set with a minimally invasive procedure. The bone fragments are grasped with a medical instrument introduced into the body of the patient and are subsequently set. Medical instruments suitable for setting bone fragments are described and shown, for example, in Irmengard Middelanis, Marget Liehn, Lutz Steinmüller, Rüdiger Döhler (Editors), OP-Handbuch, Grundlagen Instrumentation OP-Ablauf, Springer Verlag, Berlin, Heidelberg 1995, pages 159 and 160. The movement of the medical instrument during the intervention can be tracked with the known and above-described medical devices by mixing the image of the medical instrument into the image of the body of the patient. However, a visualization of the position of the bone fragments modified as a result of the setting is not possible with such a known system.

German OS 100 57 023 discloses providing an imaged bone fragment with a marking in a volume dataset formed by a series of 2D projections of a bone fracture acquired from different projection directions. For assisting the physician treating the bone fracture, the marking is subsequently mixed into at least one of the 2D projections.

SUMMARY OF THE INVENTION

It is an object of the invention to provide a medical apparatus with which an image of a moved bone fragment can be produced.

This object is achieved in accordance with the invention in a medical apparatus having a data processing device for storing an image dataset of the body of a subject and to which a viewing device for visualizing the image represented by the image dataset is at least indirectly connectable, an image computer means for segmenting at least one bone fragment of the subject presented in the image, a medical instrument for introduction into the body of the subject, the bone fragment presented segmented in the image being graspable with the end of the medical instrument introduced into the body and being movable with the medical instrument. A navigation system determines the position of the medical instrument relative to the body of the subject while the bone fragment is being moved with the medical instrument, and the data processing device identifies the modified position of the bone fragment on the basis of the position of the medical instrument relative to the body of the subject identified with the navigation system, and displays the segmented presentation of the bone fragment in the image in conformity with the modified position of the bone fragment.

If the image dataset is produced with an X-ray device, according to an embodiment of the invention, then the data processing device can be, for example, an image computer of the X-ray device. For example, a physician can view the image allocated to the image dataset with the viewing device that is at least indirectly connectable to the data processing device, said image being an X-ray image when the image dataset is acquired with an X-ray device. The physician can segment individual bone fragments of the life form imaged in the image with the image computer included in the inventive medical apparatus. As used herein "segmenting" means an identification and outlining and/or demarcation of the contours of image excerpt of interest. US 2001/0055016 is an example of a document that discloses methods for segmenting individual image excerpts.

After the segmenting of the bone fragment, the physician can plan and simulate the intervention needed for the setting of the bone fragment.

Subsequently, the physician introduces the medical instrument into the body of the life form in order to grasp the bone fragment, the image of which was previously segmented with the medical instrument. Additionally, the image of the medical instrument, the position of which is determined with the navigation system, can be mixed into the image of the body of the subject for a targeted grasping of the bone fragment.

As a result of grasping the bone fragment with the medical instrument, the bone fragment substantially rigidly connected to the medical instrument, so that it can be moved with the medical instrument for being set. Since, moreover, the spatial extent and—due to the navigation system—the position of the medical instrument relative to the body of the subject are known, the position of the bone fragment moved with the medical instrument is also known relative to the body of the subject. It is therefore possible to update the position of the bone fragment, as it is modified due to the movement, in the image of the body of the subject. The physician thus obtains a current image of the body of the subject and of the modified position of the moved bone fragment without having to constantly produce a new X-ray image of the body of the subject.

The inventive medical apparatus particularly can assist the physician in the setting of the bone fragment when the image dataset is a volume dataset, as is the case in a preferred embodiment of the invention.

The image dataset also can be acquired from multiple 2D projection images, as in a further embodiment of the invention. The multiple 2D projections preferably are orthogonal.

If the image data set is pre-operatively produced, according to an embodiment of the invention, then a registration is undertaken in a version of the invention before the determination of the position of the medical instrument relative to the body of the subject.

Preferably, however, the image dataset is intra-operatively produced.

Particularly in the case of an intra-operatively produced image dataset, the medical apparatus in a further version of the invention has a C-arm X-ray device for producing the image dataset. The position of the C-arm of this X-ray device is simultaneously acquired together with the position of the medical instrument.

According to a further embodiment of the invention, the medical apparatus has a reference element that is arranged at the subject and with which the position of the subject can be acquired simultaneously with the position of the medical instrument. This allows the modified position of the bone fragment to be identified with adequate precision even given a movement on the part of the subject.

DESCRIPTION OF THE DRAWINGS

An exemplary embodiment of the invention is shown in the schematic FIGURE.

DESCRIPTION OF THE PREFERRED EMBODIMENTS

The FIGURE shows a C-arm X-ray device 1 that has a cart 3 movable on wheels and a lifting mechanism 4 (shown schematically in the FIGURE) with a column 5 in the exemplary embodiment. A holder 6 at which a holding mechanism for supporting a C-arm 8 is arranged, is disposed at the column 5. Opposite one another, an X-ray radiator 9 and an X-ray receiver 10 are arranged at the C-arm 8. In the exemplary embodiment, the X-ray receiver 10 is a known solid-state detector, however, the X-ray receiver 10 also can be an X-ray image intensifier. The X-ray images acquired with the solid-state detector can be presented on a display device 11 in a known way.

The C-arm X-ray device 1 shown in the FIGURE produces volume datasets, i.e. 3D X-ray images, of the body or of body parts of a patient P placed on a vertically and horizontally displaceable patient bed 12. For 3D imaging, an image computer 13 that is connected (in a way that is not shown) to the solid-state detector 10 and the display unit 11 is arranged in the cart 3 of the C-arm X-ray device 1 in the exemplary embodiment. In a manner known, the image computer 13 uses 2D projections, which are acquired given movement of the C-arm 8 along its circumference around an body part P of the patient, to reconstruct the volume dataset of the body part to be presented and causes the volume dataset to be visualized on the display unit 11 as an X-ray image 14.

In the exemplary embodiment, the X-ray image 14 is an X-ray image of a broken thighbone K of the patient P. The broken thighbone K is only partially indicated in the FIGURE. In the exemplary embodiment, the broken thighbone K of the patient P has a bone fragment F, the image 14*a* of which is shown in the X-ray image 14. The bone fragment is to be set during a medical intervention with a medical instrument 22 introduced into the body of the patient P. Suitable medical instruments are, for example, repositioning forceps or general bone instruments are shown inter alia in Irmengard Middelanis, Marget Liehn, Lutz Steinmüller, Rüdiger Döhler (Editors), OP-Handbuch, Grundlagen Instrumentation OP-Ablauf, Springer Verlag, Berlin, Heidelberg 1995, pages 159 and 160.

The image computer 13, further, is configured in the exemplary embodiment so that individual image excerpts, in particular the image 14*a* of the bone fragment F of the X-ray image 14, can be segmented. To that end, a mark 14*b* mixed into the X-ray image 14 is moved with a computer mouse 15 connected to the image computer 13 to the image 14*a* of the bone fragment F to be segmented.

The actual segmenting of the picture elements allocated to the image 14*a* of the bone fragment F is initiated in the exemplary embodiment by activating a key (not shown in the FIGURE) of the computer mouse 15 as soon as the mixed-in mark 14*b* is at the image 14*a* of the bone fragment F. The actual segmenting event is controlled by the image computer 13 according to methods known to those skilled in the art, by a computer program running on the image computer 13 analyzing the grayscale values of the volume dataset allocated to the X-ray image 14 and acquiring the contour (outline) of the image 14*a* of the bone fragment on the basis of the analysis. After the segmenting of the image 14*a* of the bone fragment F, the contours of the image 14*a* are designated in black in the exemplary embodiment.

The FIGURE also shows an optical navigation system having cameras 16, 17 and reference elements 18 through 20 that are arranged at instruments or objects to be acquired in terms of their position and that are picked up by the cameras 16, 17. A computer 21 of the navigation system evaluates the images acquired with the cameras 16, 17 and can determine the positions in space, i.e. the locations and orientations, of the reference elements 18 through 20, and thus of the instruments or objects on the basis of the acquired reference elements 18 through 20.

In the exemplary embodiment, the reference element 18 is arranged at the medical instrument 22, the reference element is arranged at the C-arm X-ray device 1 and the reference element 20 is arranged at a part of the broken thighbone K. In this way, the computer 21 can determine the respective current positions of the medical instrument 22, the C-arm X-ray device 1 and the broken thighbone K on the basis of the acquired camera images. The computer 21, which is connected to the image computer 13, makes the data about the current positions of the medical instrument 22, the C-arm X-ray device 1 and the thigh bone K available to the image computer 13, so that the image computer 13 can determine the exact location and orientation of the medical instrument 22 relative to the operation site and can mix an image 23 of the medical instrument 22 into the X-ray image 14 acquired with the C-arm X-ray device 1. A registration procedure usually is required at the beginning of the mix-in of the image 23 of the medical instrument 22. The initial position of the medical instrument 22 relative to the operation site as well as the position of the C-arm X-ray device 1 are acquired in such a registration procedure. All further movements of the medical instrument 22 and of the C-arm X-ray device 1 as well as a potential movement of the patient P (or of the patient's thigh and thus of the thigh bone K) are simultaneously and continuously acquired via the cameras 16, 17 and the computer 21. Changes in the positions of the medical instrument 22, of the C-arm X-ray device 1 or of the thigh bone K thus are virtually immediately available to the image computer 13, so that the image computer 13 can adapt the mixing of the image 23 of the medical instrument 22 into the X-ray image 14 acquired with the C-arm X-ray device 1 online, in conformity with the modified situation. In this way, not only static but also continuously successive X-ray images 14, with the mixed-in image 23 of the medical instrument 22, can be generated.

In the exemplary embodiment, a physician (not shown in the FIGURE) produces the X-ray image 14 of the patient P with the C-arm X-ray device 1 before the medical intervention. In the exemplary embodiment, the physician subsequently plans the impending medical intervention by the physician simulating a movement of the bone fragment F required for the setting of the bone fragment F. To this end, the physician simulates the path on which the bone fragment F should be moved with the medical instrument 22 during setting, by the physician moving the mixed-in mark 14b to the segmented image 14a of the bone fragment F, activating the key of the computer mouse 15 as soon as the mark 14b has been brought to the image 14a, and moving the image 14a by moving the computer mouse 15 with the key of the computer mouse 15 activated. When the physician has found a favorable path, this is stored in the image computer 13.

Subsequently, the physician introduces the medical instrument 22 into the body of the patient P and grasps the bone fragment F to be set with the end introduced into the body of the patient P. While the physician introduces the medical instrument into the body of the patient P, he/she can select whether the image 23 of the medical instrument 22 should be mixed into the X-ray image 14 in the present exemplary embodiment.

When the physician has grasped the bone fragment F with the medical instrument 22, the bone fragment F is substantially rigidly connected to the medical instrument 22, so that the bone fragment F can be moved with the medical instrument 22. Further, the spatial expanse of the medical instrument 22 is known, and changes in the position of the medical instrument 22, the C-arm X-ray device 1, or the thigh bone K are virtually immediately available in the image computer 13. Particularly on the basis of the modified position of the medical instrument 22, the image computer 13 can calculate the modified position of the bone fragment F during the setting and can update the image 14a of the bone fragment F in the X-ray image 14 according to the movement of the bone fragment F. The modified display of the image 14a of the bone fragment F can ensue either continuously, i.e. in quasi-real time, or controlled by a trigger signal.

An optical navigation system need not necessarily be utilized as the navigation system, as in the exemplary embodiment. Magnetic navigation systems are also particularly suited for determining the positions of the instrument 22, the C-arm X-ray device 1 and the thighbone K.

The positions of the medical instrument 22, the C-bend X-ray device 1 and of the thigh bone, moreover, need not be simultaneously acquired.

The determination of the positions of the C-arm X-ray device 1 and of the thighbone K need not ensue by means of the described navigation system. The positions can also be determined with other suitable means for position acquisition that, for example, operate on the basis of signal-carrying waves.

The volume dataset allocated to the X-ray image 14 need not necessarily be stored in the image computer 13 of the C-arm X-ray device 1. Alternatively, it can be stored in an external data processing device.

The image dataset need not necessarily be produced with a C-arm X-ray device 1. Other X-ray devices or means for generating an image dataset that do not employ X-rays are likewise possible. The image dataset can be a two-dimensional image dataset or can be acquired from (preferably orthogonal) multiple 2D projection images.

The volume dataset for the X-ray image 14 can be pre-operatively produced, for example with a computed tomography apparatus. For the determination of the position of the medical instrument, and thus of the bone fragment, it is necessary to make a spatial transformation of the coordinates (indicated with respect to a first coordinate system) of the position sensor of the navigation system, arranged at the medical instrument in a defined way, into the spatial coordinates of the image of the patient that is acquired with the means for generating an image dataset, and that is employed for the navigation. This transformation is referred to as registration. Markers can be attached to the patient for the registration. The positions of the markers are identified in the first coordinate system with the position sensor of the navigation system, and are identified (for example, by manual entry with an input device) in the coordinate system of the image stored in a data processing device that is acquired with the computed tomography apparatus and employed for navigation. Ultimately, a transformation can be calculated from the two point sets of the markers identified in the first coordinate system and in the coordinate system of the image employed for navigation. This transformation transforms the positions of the medical instrument acquired in the first coordinate system with the position sensor of the navigation system into the coordinates of the image during the navigation.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical apparatus comprising:
    a data processor in which an image dataset of a body region of a subject is stored, said subject containing a bone fragment and said bone fragment being represented in said image dataset;
    a display connected to said data processor that displays an image of the body region, obtained from said image dataset, said image containing a visualization of said bone fragment;
    an image computer connected to said data processor that executes a segmentation procedure to produce a segmented visualization of said bone fragment in said image allowing said segmented visualization of said bone fragment to be repositioned in said image of said body region on said display of the body region;

a medical instrument configured for introduction into the body of the subject and configured to interact with said bone fragment in the body of the subject to move said bone fragment;

a navigation system that determines a position of the medical instrument relative to the body of the subject while said bone fragment is being moved with said medical instrument, and that generates medical instrument position data representing said position; and said data processor being connected to said navigation system and being supplied with said medical instrument position data and determining, solely from said medical instrument position data, a modified position of the bone fragment relative to the body of the subject, and causing said segmented visualization of said bone fragment to be repositioned in said image of said body region on said display in conformity with said modified position as said bone fragment is moved by said medical instrument.

2. A medical apparatus as claimed in claim 1 comprising an X-ray apparatus for producing said image dataset.

3. A medical apparatus as claimed in claim 2 wherein said X-ray apparatus generates a volume dataset as said image dataset.

4. A medical apparatus as claimed in claim 2 wherein said X-ray apparatus produces a plurality of two-dimensional projection images forming said image dataset.

5. A medical apparatus as claimed in claim 2 wherein said X-ray apparatus is a C-arm X-ray apparatus having a movable C-arm, and wherein said C-arm X-ray apparatus generates said dataset, by moving said C-arm, intra-operatively while said bone fragment is being moved by said instrument, and wherein data representing a position of said C-arm are generated and supplied to said data processor.

6. A medical apparatus as claimed in claim 1 comprising a reference element adapted for arrangement at said subject, said reference element being detectable by said navigation system and said navigation system generating data representing said position of said reference element together with said medical instrument position data while said bone fragment is being moved by said medical instrument.

7. A medical apparatus as claimed in claim 1 wherein said navigation system generates said medical instrument position data intra-operatively while said medical instrument is moving said bone fragment, without a registration.

8. A method for displaying a movable bone fragment disposed in a body of a subject, comprising the steps of:

generating an image dataset of a body region of a subject containing a movable bone fragment;

from said image dataset, generating and displaying an image of the body region of the subject containing a visualization of said bone fragment;

executing a segmentation procedure to produce a segmented visualization of said bone fragment in said image of the body region allowing said segmented visualization of said bone fragment to be repositioned in said image of said body region;

introducing a medical instrument into the body of the subject to move the bone fragment in the body;

using a navigation system, monitoring a position of the medical instrument relative to the body of the subject as said medical instrument is being moved, and generating medical instrument position data; and directly and solely from said medical instrument position data, determining a modified position of the bone fragment in the body of the subjects, and repositioning said segmented presentation of said bone fragment in said image of the body region in conformity with said modified position as said bone fragment is moved by said medical instrument.

9. A method as claimed in claim 8 comprising generating said image dataset with an X-ray apparatus.

10. A method as claimed in claim 8 comprising generating a volume dataset as said image dataset.

11. A method as claimed in claim 8 comprising generating a plurality of two-dimensional projection images of the body of the subject as said image dataset.

12. A method as claimed in claim 8 comprising generating said image dataset pre-operatively, before introduction of said medical instrument into the body of the subject.

13. A method as claimed in claim 12 comprising undertaking a registration with said navigation system before beginning monitoring of the position of the medical instrument relative to the body of the subject.

14. A method as claimed in claim 8 comprising generating said image dataset intra-operatively, after introducing the medical instrument into the body of the subject.

15. A method as claimed in claim 14 comprising generating said image dataset using a C-arm X-ray apparatus having a movable C-arm, and simultaneously identifying a position of said C-arm together with monitoring the position of the medical instrument.

16. A method as claimed in claim 14 comprising arranging a reference element, detectable by said navigation system, at said subject and simultaneously monitoring a position of the subject together with monitoring the position of the medical instrument.

17. A method as claimed in claim 14 comprising, with said navigation system, monitoring the position of the medical instrument without a previous registration.

* * * * *